United States Patent
Zucchi et al.

(10) Patent No.: US 8,714,973 B2
(45) Date of Patent: May 6, 2014

(54) INTERACTIVE/PASSIVE BRACKET SYSTEM

(76) Inventors: Temistocles Uriarte Zucchi, Erechim (BR); Chune Avruch Janovich, Porto Alegre (BR)

( * ) Notice: Subject to any disclaimer, the term of this patent is extended or adjusted under 35 U.S.C. 154(b) by 0 days.

(21) Appl. No.: 13/396,706

(22) Filed: Feb. 15, 2012

(65) Prior Publication Data

US 2012/0208143 A1     Aug. 16, 2012

(30) Foreign Application Priority Data

Feb. 15, 2011   (BR) .................................... 1100503

(51) Int. Cl.
    *A61C 3/00*      (2006.01)
(52) U.S. Cl.
    USPC .................................. 433/11; 433/8
(58) Field of Classification Search
    USPC .................................. 433/8–16, 24
    See application file for complete search history.

(56) References Cited

U.S. PATENT DOCUMENTS

| | | | |
|---|---|---|---|
| 3,748,740 A | 7/1973 | Wildman | |
| 3,772,787 A | 11/1973 | Hanson | |
| 3,775,850 A * | 12/1973 | Northcutt | 433/16 |
| 4,103,423 A * | 8/1978 | Kessel | 433/10 |
| 4,248,588 A * | 2/1981 | Hanson | 433/11 |
| 4,492,573 A * | 1/1985 | Hanson | 433/11 |
| 5,429,500 A | 7/1995 | Damon | |
| 5,474,445 A * | 12/1995 | Voudouris | 433/10 |
| 5,562,444 A * | 10/1996 | Heiser et al. | 433/11 |
| 5,586,882 A * | 12/1996 | Hanson | 433/13 |
| 5,700,145 A | 12/1997 | Wildman | |
| 5,906,486 A * | 5/1999 | Hanson | 433/11 |
| 6,071,119 A * | 6/2000 | Christoff et al. | 433/14 |
| 6,168,428 B1 * | 1/2001 | Voudouris | 433/11 |
| 6,257,883 B1 * | 7/2001 | Voudouris | 433/11 |
| 6,368,105 B1 | 4/2002 | Voudouris et al. | |
| 6,659,767 B2 * | 12/2003 | Abels et al. | 433/10 |
| 6,843,651 B2 * | 1/2005 | Orikasa | 433/13 |
| 7,186,114 B2 * | 3/2007 | Navarro et al. | 433/11 |
| 7,267,545 B2 | 9/2007 | Oda | |
| 7,686,613 B2 | 3/2010 | Pospisil et al. | |
| 7,963,768 B2 * | 6/2011 | Hilliard | 433/11 |
| 7,967,603 B2 * | 6/2011 | Heiser | 433/10 |
| 8,246,348 B2 * | 8/2012 | Heiser | 433/10 |
| 2002/0110773 A1 * | 8/2002 | Abels et al. | 433/10 |
| 2002/0110775 A1 * | 8/2002 | Abels et al. | 433/11 |
| 2002/0110776 A1 * | 8/2002 | Abels et al. | 433/11 |
| 2002/0110777 A1 * | 8/2002 | Abels et al. | 433/11 |
| 2002/0110778 A1 * | 8/2002 | Abels et al. | 433/11 |
| 2005/0019719 A1 * | 1/2005 | Hanson | 433/10 |
| 2009/0061376 A1 * | 3/2009 | Wool | 433/11 |
| 2010/0151403 A1 * | 6/2010 | Tuneberg et al. | 433/10 |
| 2010/0203463 A1 * | 8/2010 | Huff et al. | 433/10 |
| 2012/0129120 A1 * | 5/2012 | Foerster | 433/11 |

* cited by examiner

OTHER PUBLICATIONS

PCT/US1982/000682 ; WO8203979 ; EP 0079376 ; http://www.wipo.int/patentscope/search/en/detail.jsf?docId=WO1982003979&recNum=1&docAn=US1982000682&queryString=FP:%28WO8203979%29&maxRec=1.

*Primary Examiner* — Hao D Mai
(74) *Attorney, Agent, or Firm* — Patent Law Agency, LLC; Peter Ganjian

(57) ABSTRACT

Interactive/passive bracket system developed to provide orthodontic treatment in a more comfortable, efficient and faster manner. Its function with the orthodontic wire may be determined by an orthodontist in order to make it interactive or only passive. It is something innovative because no bracket system can provide these two features in the same bracket. The presence of two convertible slots which is also a significant differential feature will simplify the tooth movement in the class I, II and Angle III relations. Besides, the rounded design makes the Revolution systems more comfortable and traps less food, thus facilitating brushing.

7 Claims, 1 Drawing Sheet

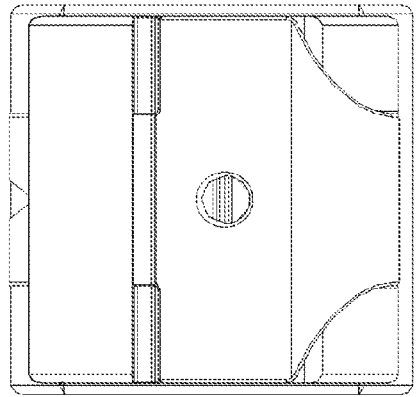
FIG. 2
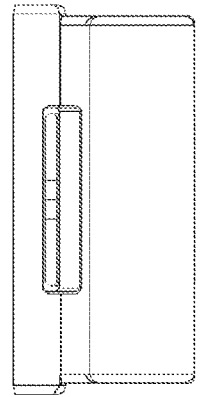
FIG. 3
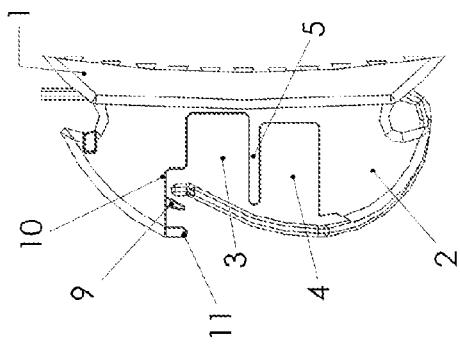
FIG. 4
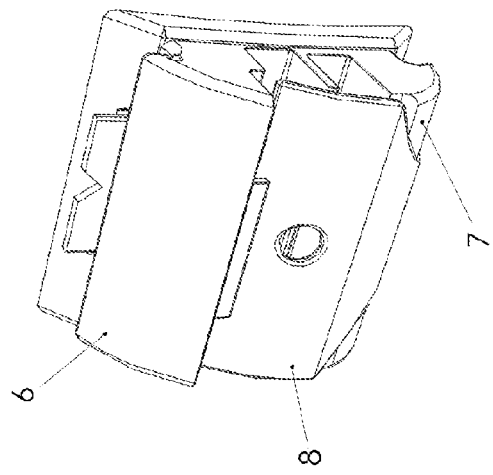
FIG. 1
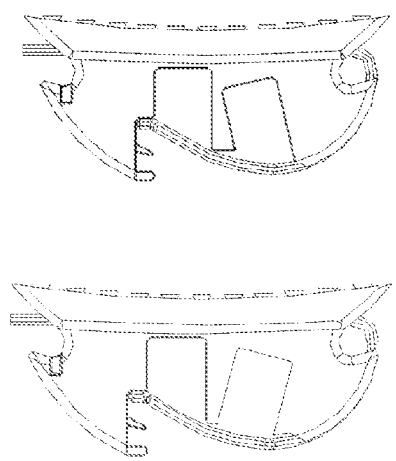
FIG. 6
FIG. 5

INTERACTIVE/PASSIVE BRACKET SYSTEM

CROSS-REFERENCE TO RELATED APPLICATIONS

This is a CONTINUATION application that claims the benefit of foreign priority of the co-pending Federal Republic of Brazil Patent Application No. PI 1100503-3, with a filing date of 15 Feb. 2011, the entire disclosures of which Application is hereby expressly incorporated by reference herein.

BACKGROUND OF THE INVENTION

1. Field of the Invention

This descriptive report of the invention refers to a bracket system developed to serve as an auxiliary means in orthodontic treatment, thus creating different possibilities in applied mechanics. An orthodontist may determine both its function and its relation with the wire in order to make it interactive or only passive. It is innovative because no bracket system has managed to provide these two features in the same bracket system so far. The presence of two slots which is also a significant differential feature makes various movements easier, its shape reduces discomfort reported by patients, and it is more hygienic.

2. Description of Related Art

The Boyd band bracket was the first self-ligating mechanism designed and patented by Charles E. Boyd in 1933. The Russell Lock bracket described by Stolzenberg in 1935 followed soon afterwards. The Russell Lock bracket could be opened and closed. A special key was necessary to make adjustments. Source: Berger (2011).

A little time later, James W. Ford designed the Ford adapter which was abandoned afterwards. His son began to manufacture it again in 1951. From that moment on there was big interest in this kind of self-ligating brackets, albeit without big success. A breakthrough occurred only in the 1970s, more precisely in 1971, when Alexander J. Wildman designed the Edgelock bracket (U.S. Pat. No. 3,748,740). It was a round bracket with a rigid rotating cover which passively closed the slot.

Other models followed, the main one being the Mobile lock. This concept was not well received due to its bulky design, limited control over teeth and elastic ligatures widely used by orthodontists at that time.

In the mid 70's, the SPEED bracket (U.S. Pat. No. 3,772,787), which represented the beginning of a new era for self-ligating brackets as it was an active one. But it became available on the market for the first time only in 1981.

In 1986, the Activa brackets designed by E. Pletcher (WO/1982/003979) were made available as an alternative to conventional ligation systems. Said bracket system featured a rigid circular clip that rotated in an occlusogingival direction around the cylindrical body of the bracket, thus forming a passive tube which was easily opened by a patient.

The Time bracket marketed in 1995 came next in the sequence of self-ligating bracket systems in which the clip was made from a rigid and curved material which, when closed, wrapped around the vestibular surface of the bracket body. The stiffness of this active cover prevented any interaction with the archwire, thereby rendering it a passive bracket system.

The Damon SL (U.S. Pat. No. 5,429,500), a passive system, was introduced a year later, in 1996. The TwinLock bracket developed by A. J. Wildman (U.S. Pat. No. 5,700,145) who also had designed the Edgelock, entered the marketplace in 1998.

A year later, the TwinLock bracket was modified and named Damon 2 (a passive system), and Damon 3 (U.S. Pat. No. 7,267,545), a hybrid passive bracket made from metal and composite resin, was designed in 2004.

BIRNIE (2008) reports that since its introduction the design of the Damon bracket has featured a passive self-ligating design, conventional ties, and a cover with a positive passive mechanism to keep it open or closed. As the bracket kept evolving, its features changed as well: it became smaller with a lower profile and rounded contours providing more comfort to patients. As a result of clearer understanding of the function of the bracket and advances in manufacturing technologies, the mechanism of the cover became safer and simpler to open and close.

In 2000, GAG introduced In-Ovation bracket (U.S. Pat. No. 6,368,105) which was bulkier than SPEED bracket and featured an active Elgiloy clip different from the SPEED nickel titanium clip whose elasticity of the material was larger.

In 2004, the passive Smartclip bracket was introduced (U.S. Pat. No. 7,686,613) while Damon 3MX was launched in 2005 and followed in 2006 by Quick Bracket by Forestadent (a German company) whose action of the clip was active.

BRIEF SUMMARY OF THE INVENTION

The bracket proposed herein has the following advantages:

Its rounded shape is more comfortable for the patient since the tie-wings which actually function as active tips injuring the patient's mucosa were removed. Moreover it is more hygienic due to its shape and removal of likely sites of plaque accumulation.

It features two slots both of which become totally exposed when the clip is open;

It may be interactive or only passive, depending on the treatment stage and type of desired movement;

The removal of the hook is compensated by the presence of a slot in the part directed to the cervical of the bracket designed to retain the elastics in intercuspal mechanics and Class II and Class III corrections;

Customized brackets for compensatory corrections class II and class III can be disposed in the secondary slot.

The developed bracket features 4 variations:

Revolution Standard: main and secondary slots in the straight-wire prescription.

Revolution Edgewise: main slot— straight-wire prescription and a secondary slot— Edgewise prescription.

Revolution II: main slot— straight-wire prescription and secondary slot with torque for class II.

Revolution III: main slot— straight-wire prescription and secondary slot with torque for class III.

The invention may be more fully understood by reference to the following drawings representative of the interactive/passive bracket system so that the device can be fully reproduced by an adequate technique allowing full characterization of the functionality of the claimed object.

The descriptive part of the report is based on the drawings that express the best or preferred mode of carrying out the conceived product through the detailed and consecutive numeration which clarifies the aspects that may be implied by the adopted representation in order to clearly determine the protection intended herein.

The drawings are purely illustrative and may vary since they do not deviate from the scope of this invention.

BRIEF DESCRIPTION OF THE DRAWINGS

FIG. 1 is a perspective view of the Standard Revolution and Revolution Edgewise bracket;

FIG. 2 is a front view of the bracket;
FIG. 3 is a view from above;
FIG. 4 is a side view;
FIG. 5 is a side view of the Revolution II bracket; and
FIG. 6 is a side view of the Revolution III bracket.

DETAILED DESCRIPTION OF THE INVENTION

The developed orthodontic device refers to a part called bracket. This part is used for tooth movement during orthodontic treatment. At present brackets use a metallic clip system which dispenses with the use of colored rubber bands (elastics) to keep the orthodontic wire inside the slot. Such devices are called self-ligating and provide a faster, more comfortable and hygienic treatment. The self-ligating brackets in the marketplace now are passive or interactive and each has different functions. The bracket proposed herein is an innovative system as it uses both systems interactive and active because, depending on the treatment stage, the clip may act either interactively ensuring greater action of the clip over the wire or passively when there is no clip over the wire.

Another feature that makes the system different from the rest of self-ligating brackets is a second slot (secondary slot) which can become convertible (exposed) when the clip is totally opened. Due to this opening of the secondary slot, which facilitates the insertion of an orthodontic wire, the torque will be only in this slot in case of Angle classes II and III. Besides, this bracket has an innovative design which is more rounded, thus trapping less food and facilitating oral hygiene, and making the treatment more comfortable.

This feature is found only in the bracket proposed herein aiming at facilitating the insertion of orthodontic wires, thus creating innumerous possibilities of tooth movement.

The bracket proposed herein comprises a base for fixation on the tooth (1), which is part of the main structure or body (2) containing two slits or a main slot (3) and a secondary slot (4) separated from each other by a wall (5); an orthodontic wire (not shown) may be introduced into each of said slots where said slots may be closed by a clip (8), said bracket further containing un upper wing (6) and a lower wing (7).

The clip (8) may act interactively between 9 and 10 and passively between 9 and 11 where (9) represents the stop of the clip.

What is claimed is:
1. A bracket, comprising:
a base;
the base is adapted to be coupled with a tooth;
a main structure associated with the base; and
a clip having a passive mode of operation and an interactive mode of operation to selectively affect change in mechanical forces experienced by the tooth when the clip is in closed position;
in the closed position, a first free end of the clip extends out from the bracket, with a second free end that moves to one of passive mode of operation and interactive mode of operation positions;
the main structure is comprised of a first, a second, and a third portions positioned along a height of the bracket;
the first portion of the main structure includes:
a first tie wing that extends longitudinally along an axial length of the bracket and includes a first curved profile to form a first curved surface for comfort and improved hygiene;
a first end of the first curved profile includes a first apex portion, below which first apex portion is a channel that extends longitudinally along the axial length of the bracket and is positioned behind the first curved surface;
a surface of the first portion includes:
a first retaining flange that extends substantially vertically from a second end of the first curved surface;
a second retaining flange slanted at an angle and positioned behind the first retaining flange toward the base; and
a stop wall;
with a first spacing formed between the first retaining flange and the second retaining flange constituting a passive mode spacing for the passive mode of operation of the clip when the second free end of the clip is positioned within the formed first spacing, and a second spacing formed between the second retaining flange and the stop wall constituting an interactive mode spacing for the interactive mode of operation of the clip when the second free end of the clip is positioned within the formed second spacing;
a second portion of the main structure includes:
a first slot that extends longitudinally along the axial length of the bracket;
a second slot extending longitudinally along the axial length of the bracket;
the first and second slots are positioned generally centrally in relation to the height of the bracket and adjacent and parallel one another, separated by a wall flange common to both the first and the second slots;
the first slot and a first slot opening of the first slot is oriented in a same direction as the second slot and a second slot opening of the second slot;
the third portion of the main structure includes:
a second tie wing that includes a second curved profile that extends longitudinally along the axial length of the bracket to form a second curved surface for comfort and improved hygiene;
a first end of the second curved profile includes a second apex portion, behind which is a curved channel that extends longitudinally along the axial length of the bracket; and
a second end of the second curved profile includes a curved indentation.
2. The bracket as set forth in claim 1, wherein:
the clip includes an opening aperture.
3. The bracket as set forth in claim 1, wherein:
the base is part of the main structure.
4. A bracket, comprising:
a base;
the base is adapted to be coupled with a tooth;
a main structure associated with the base; and
a clip having a passive mode of operation and an interactive mode of operation to selectively affect change in the mechanical forces experienced by the tooth when the clip is in closed position;
the main structure includes:
a first slot that extends longitudinally along an axial length of the bracket that is covered by the clip in a clip closed position;
a second slot extending longitudinally along the axial length of the bracket that is covered by the clip in the clip closed position;
the first and second slots are positioned centrally in relation to the height of the bracket and adjacent and parallel one another, separated by a wall flange common to both the first and the second slots;
the first slot and a first slot opening of the first slot is oriented in a same direction as the second slot and a second slot opening of the second slot
a first spacing formed between a first retaining flange and a second retaining flange constituting a passive mode spacing for the passive mode of operation of the clip when a second free end of the clip is positioned within the formed first spacing, and a second spacing formed between a second retaining flange and a stop wall constituting an interactive mode spacing for the interactive mode of operation of the clip when the second free end of the clip is positioned within the formed second spacing.

5. A bracket, comprising:
a base;
the base is adapted to be coupled with a tooth;
a main structure associated with the base and includes first and second slots with first and second slot openings; and
a clip having a passive mode of operation and an interactive mode of operation to selectively affect change in the mechanical forces experienced by the tooth when the clip is in closed position over the first and second slot openings;
in the closed position, the clip includes a first free end extending out from the bracket, and a second free end that resiliently articulates to one of passive mode of operation and interactive mode of operation positions;
the main structure is comprised of a first portion that includes:
a surface that is comprised of:
a first retaining flange that extends substantially vertically from a second end of an upper curved surface;
a second retaining flange that is positioned behind the first retaining flange toward the base; and
a stop wall;
with a first spacing formed between the first retaining flange and the second retaining flange constituting a passive mode spacing for the passive mode of operation of the clip when the second free end of the clip is positioned within the formed first spacing, and a second spacing formed between the second retaining flange and the stop wall constituting an interactive mode spacing for the interactive mode of operation of the clip when the second free end of the clip is positioned within the formed second spacing.

6. A bracket, comprising:
a base;
the base is adapted to be coupled with a tooth;
a main structure associated with the base; and
a clip;
the main structure includes:
a first slot and a first slot opening of the first slot that is oriented in a same direction as a second slot and a second slot opening of the second slot; and
a first retaining flange that extends from a second end of a first curved surface; and
a second retaining flange that is slanted at an angle away from the base and positioned behind the first retaining flange toward the base;
with first and second retaining flanges defining a first and a second spacing for respective passive and interactive modes of operation of the clip when the clip is in closed position, closing the first and second slots;
with the first spacing formed between the first retaining flange and the second retaining flange constituting a passive mode spacing for the passive mode of operation of the clip when a second free end of the clip is positioned within the formed first spacing, and a second spacing formed between the second retaining flange and a stop wall constituting an interactive mode spacing for the interactive mode of operation of the clip when the second free end of the clip is positioned within the formed second spacing.

7. A bracket, comprising:
a base;
the base is adapted to be coupled with a tooth;
a main structure associated with the base; and
a clip;
the main structure includes:
a first slot and a first slot opening of the first slot that is oriented in an angle in relation to a second slot and a second slot opening of the second slot; and
a first retaining flange that extends from a second end of a first curved surface; and
a second retaining flange that is slanted at an angle away from the base and positioned behind the first retaining flange toward the base;
with first and second retaining flanges defining a first and a second spacing for respective passive and interactive modes of operation of the clip when the clip is in closed position, closing the first and second slots;
with the first spacing formed between the first retaining flange and the second retaining flange constituting a passive mode spacing for the passive mode of operation of the clip when a second free end of the clip is positioned within the formed first spacing, and the second spacing formed between the second retaining flange and a stop wall constituting an interactive mode spacing for the interactive mode of operation of the clip when the second free end of the clip is positioned within the formed second spacing.

* * * * *